United States Patent [19]
Hori et al.

[11] Patent Number: 5,359,992
[45] Date of Patent: Nov. 1, 1994

[54] ENDOSCOPE COUPLER WITH MAGNETIC FOCUS CONTROL

[75] Inventors: Koichiro Hori, Framingham; Dennis Arsenault, Ashland, both of Mass.

[73] Assignee: Linvatec Corporation, Largo, Fla.

[21] Appl. No.: 963,356

[22] Filed: Oct. 20, 1992

[51] Int. Cl.⁵ .............................................. A61B 1/00
[52] U.S. Cl. .................................... 128/4; 354/62; 403/DIG. 1; 359/903
[58] Field of Search .............. 359/903, 823, 503, 513; 358/98; 403/DIG. 1; 128/4; 354/62, 195.1; 335/306; 464/29

[56] References Cited

U.S. PATENT DOCUMENTS

| | | | |
|---|---|---|---|
| 4,152,099 | 5/1979 | Bingler | 403/DIG. 1 X |
| 4,569,333 | 2/1986 | Bel et al. | 128/4 |
| 4,611,888 | 9/1986 | Prenovitz et al. | 350/96.22 |
| 4,722,000 | 1/1988 | Chatenever | 358/98 |
| 4,740,058 | 4/1988 | Hori et al. | 350/255 |
| 4,781,448 | 11/1988 | Chatenever et al. | 350/429 |
| 4,807,594 | 2/1989 | Chatenever | 128/4 |
| 4,844,071 | 7/1989 | Chen et al. | 128/6 |
| 4,851,866 | 7/1989 | Ciarlei et al. | 354/62 |
| 4,863,304 | 9/1989 | Bauer et al. | 403/37 |
| 4,969,450 | 11/1990 | Chinnock et al. | 128/6 |
| 5,014,032 | 5/1991 | Aubert | 335/306 |
| 5,056,902 | 10/1991 | Chinnock et al. | 359/503 |
| 5,139,383 | 8/1992 | Polvak et al. | 403/DIG. 1 X |
| 5,204,572 | 4/1993 | Ferreira | 335/306 X |

FOREIGN PATENT DOCUMENTS

| | | | |
|---|---|---|---|
| 970298 | 9/1958 | Germany | 359/903 |

*Primary Examiner*—Richard J. Apley
*Assistant Examiner*—Beverly A. Meindl

[57] ABSTRACT

An endoscope coupler includes a sealed chamber and a lens assembly longitudinally movable within the chamber for focusing an image to be received by a video camera. Spaced permanent drive magnets located exteriorly of the chamber are magnetically coupled with respective permanent driven magnets secured to the lens assembly in the chamber for moving the lens assembly simultaneously with movement of the drive magnets. A focusing ring is rotatable but not longitudinally movable about the chamber and translates the drive magnets and, therefore, the driven magnets and lens assembly longitudinally in response to focusing ring rotation. Frictional retaining rings disposed between the chamber and the focusing ring resist movement of the focusing ring to provide enhanced tactile response when the focusing ring is manually moved by an operator.

18 Claims, 2 Drawing Sheets

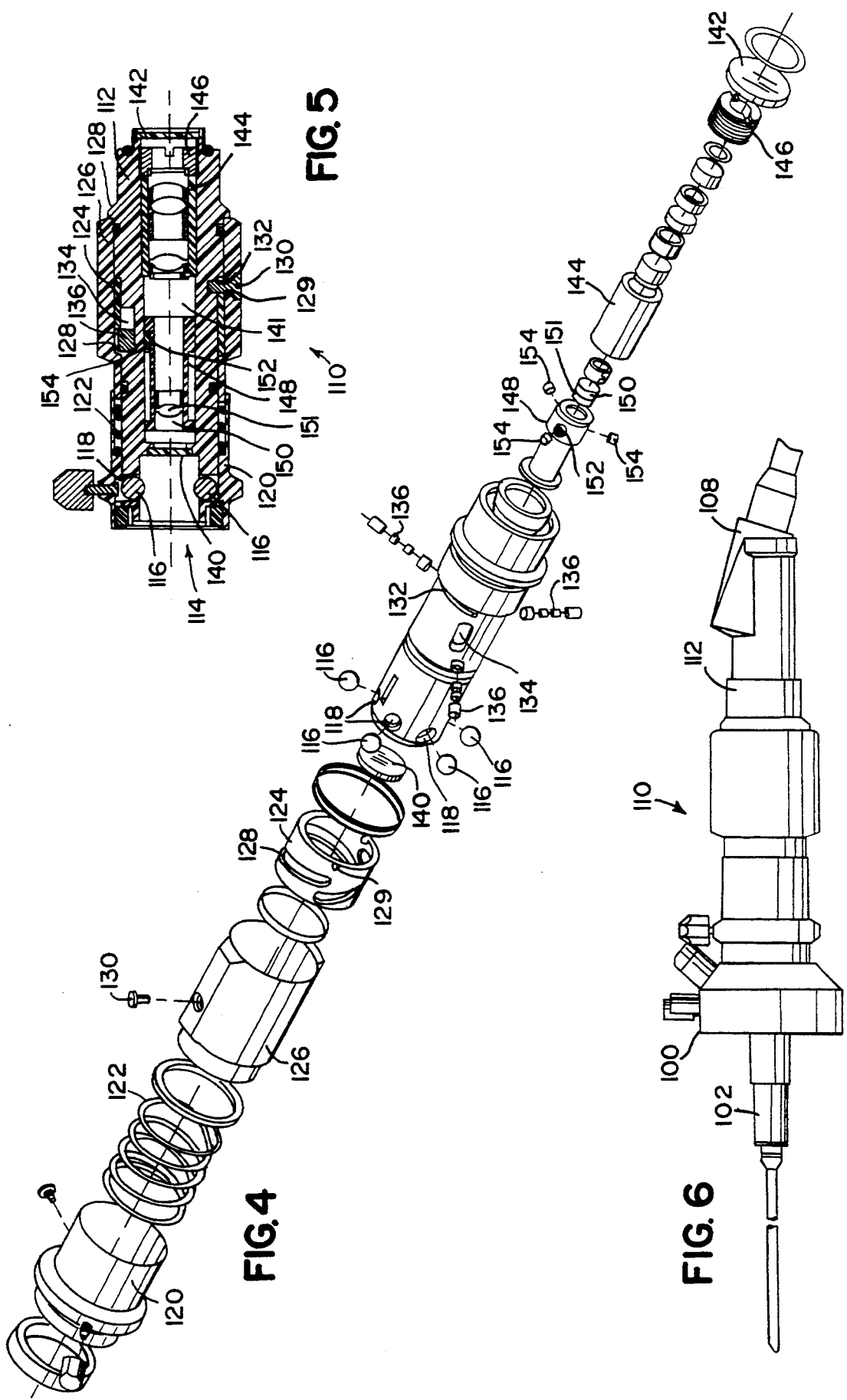

ENDOSCOPE COUPLER WITH MAGNETIC FOCUS CONTROL

BACKGROUND OF THE INVENTION

Field of the Invention

The present invention pertains to endoscope couplers for optically and mechanically coupling an endoscope to a video camera. More particularly, the invention relates to endoscope couplers having a focus control lens movable in a permanently sealed chamber.

Description of the Prior Art

Endoscopes have become widely utilized in surgery for viewing body cavities and organs to permit performance of diagnostic and surgical procedures internally without the need for invasive surgical procedures. An endoscope is typically inserted through a small incision portal providing access to the body cavity. A lens at a distal end of the endoscope is positioned to receive light reflected from a site to be observed, and images of the site can be viewed remotely to conduct histological examinations and to perform closed, or endoscopic, surgery. As used herein, the term endoscope refers generically to viewing devices for remotely observing otherwise inaccessible body cavities with minimal trauma and intrusion, including but not limited to arthroscopes, colonoscopes, bronchoscopes, hysteroscopes, cystoscopes, sigmoidoscopes, laparoscopes and ureteroscopes.

Endoscopes are sometimes supplied with an eyepiece at a proximal end thereof, and relay lenses in the endoscope typically produce an image for direct viewing through the eyepiece. However, adaptation of video camera technology to endoscopy imaging has enabled the output image of an endoscope to be viewed on a video monitor. Specifically, a video camera is electronically coupled to the video monitor and optically and mechanically coupled with the proximal end of the endoscope. Indirect or video monitor viewing of endoscopic images provides numerous benefits over direct viewing through an eyepiece, including: protection of a direct viewer's vision from high intensity illumination passed through the endoscope and reflecting off bodily tissue; enhancement of operator comfort and freedom of movement; increased endoscope utility and efficiency; reduction in the time required to conduct many endoscopic procedures; simultaneous viewing of endoscopic images by more than one person; and recordation and real time transmission of surgical procedures.

An endoscope coupler is required to couple the proximal end of the endoscope to the video camera, illustrative endoscope couplers being shown in U.S. Pat. Nos.: 4,569,333 (Bel et al); 4,611,888 (Prenovitz et al); 4,722,000 (Chatenever); 4,740,058 (Hori et al); 4,781,448 (Chatenever et al); 4,807,594 (Chatenever); 4,844,071 (Chen et al); 4,851,866 (Ciarlei et al); 4,863,304 (Bauer et al); 4,969,450 (Chinnock et al); and 5,056,902 (Chinnock et al). Endoscope couplers usually include a cylindrical body closed at opposing ends by end windows and containing a lens holder carrying one or more lenses longitudinally movable within the body to adjustably focus an image from the endoscope onto a focal plane of the camera. A focusing ring is mounted on the body and is coupled with the interior lens holder to selectively move the lens holder and the lens in response to movement of the focusing ring. Mechanical interconnection between the focusing ring and the lens holder (e.g., by cam pins on the focusing ring riding in slots in the lens holder) permit longitudinal movement of the lens holder in response to focusing ring rotation while preventing rotation of the lens holder.

In order to maintain sterile surgical conditions, endoscope couplers must be sterilized before and after each use. Prevailing methods for sterilizing surgical instruments include steam autoclaving, immersion in sterilization liquid and gas sterilization. Steam autoclaving is commonly performed under extremely high temperatures, and most endoscope couplers are unsuitable for sterilization by steam autoclaving due to their inability to withstand high temperatures without structural degradation and damage. Therefore, the preferred protocol for sterilizing endoscope couplers involves total immersion in disinfecting liquid or prolonged exposure to sterilizing gas. Because gas sterilization necessitates specialized sterilization apparatus and is usually relatively expensive, the most preferred method of sterilizing endoscope couplers involves total submersion of the endoscope coupler in sterilizing liquids, such as glutaraldehyde based solutions. Sterilization of endoscope couplers by soaking in sterilizing liquids is simple to perform, requires no highly customized equipment or specialized labor and is relatively inexpensive. However, conventional endoscope couplers are adversely affected when sterilized by submersion in disinfecting solutions or by gas sterilization. For example, the mechanical drive mechanism interconnecting the focusing ring and the lens holder in conventional endoscope couplers allows sterilizing liquid or gas to seep into the coupler body around the drive mechanism. Specifically, cam pin and slot drive mechanisms, as well as other mechanical linkages between the focusing ring and the lens holder, provide fluid communication between the interior and exterior of the coupler body. Liquid or gas entering the coupler body can create residue on and spot the end windows as well as the interior lens whereby the image presented to the video camera is significantly impaired. Even small amounts of sterilizing liquid or gas in the coupler body can produce serious consequences if deposited on the end windows and/or the lens. Further, minute residual amounts of liquid in the coupler body can produce condensation on the windows and lens during use as heat from illumination directed through the endoscope causes fogging of the relatively cooler windows and lens. Condensation on the windows and lens detracts from image clarity at the video camera and can seriously hamper diagnostic and surgical procedures. Frequently, condensation does not occur until heat from illumination produces a relatively high temperature gradient between the proximal end of the endoscope and the endoscope coupler and, by that time, the surgical procedure is usually well under way. In many cases, the procedure must be temporarily suspended to permit replacement of the endoscope coupler. Moreover, endoscope couplers known to experience problems due to residual moisture must be reconditioned through dismantling, cleaning, drying and reassembling, a process that is time consuming and absorbs scarce personnel resources. Although most conventional endoscope couplers include seals at cam and slot for preventing leakage of sterilizing fluid into the coupler body, these seals are usually O-ring or quad-ring seals that perform inadequately under fluid and gas sterilization conditions. Such seals generally fail to prevent entry of fluid or gas into the coupler body and have the further disadvantage of increasing the structural and manufacturing complexity and cost of the endoscope coupler.

It is known in the prior art to provide an endoscope coupler with a sealed chamber containing a lens focused by means of a magnetic field. Specifically, U.S. Pat. No. 5,056,092 (Chinnock et al) discloses an annular magnet disposed concentrically about the sealed chamber and arranged to move axially in response to rotation of a focusing ring. The interior focusing lens is supported in a magnetically permeable actuator housing defining a closed flux path with the exterior magnet so that the actuator housing and focusing lens are moved axially in response to axial movement of the magnet. This patent also discloses that the actuator housing may be an annular magnet. The resulting coupler structure permits the chamber containing the lens to be effectively sealed since there are no mechanical elements extending into the chamber. However, manufacture of the control arrangement is relatively expensive because each annular magnet must be custom made. More specifically, a ring magnet, once formed, cannot be machined to tailor its fit and orientation in the final assembly. The fit and orientation of the control magnet are crucial in the Chinnock et al device in order to assure accurate control over the actuation housing position. Accordingly, the magnet must be manufactured to such close tolerances as to preclude the use of mass production techniques.

Another disadvantage of many endoscope couplers is that the structure for connecting the coupler with the proximal end of an endoscope and a video camera is so complex as to make it difficult for the coupler to be attached and detached. Frequently, endoscope couplers are sterilized separately from endoscopes and video cameras, and considerable time and effort is required when complex connecting mechanisms are utilized to disconnect a coupler from an endoscope and a video camera prior to sterilization and to reattach the coupler to an endoscope and a video camera after sterilization and prior to use. Moreover, many connecting devices are limited for use with certain sizes and types of video cameras, and attachments must be utilized to adapt the endoscope couplers accordingly. Such attachments are usually difficult to apply to endoscope couplers and similarly require significant time and labor for assembly and disassembly.

A further drawback of conventional endoscope couplers is that the focusing rings commonly do not provide an acceptable tactile response with the result that the focusing rings feel too loose or too tight. Consequently, it is difficult for an operator to gain tactile control during focusing, and lack of proper "feel" detracts from the functional utility of most endoscope couplers. Until the present invention, there has been no low cost and functionally effective endoscope coupler formed water and gas-tight while allowing the focusing ring to drive the lens assembly in a tactually responsive manner without rotation of the lens assembly within the coupler.

SUMMARY OF THE INVENTION

Accordingly, it is an object of the present invention to overcome the above-mentioned disadvantages of prior art endoscope couplers.

Another object of the present invention is to provide a low cost endoscope coupler having a focusing ring for reliably moving a lens assembly axially within the coupler in response to rotation but no axial movement of the focusing ring and without mechanical interconnection of the focusing ring and the lens assembly.

A further object of the present invention is to provide a reliable low cost magnetic drive for positively moving a lens assembly longitudinally within a sealed chamber in an endoscope coupler.

It is also an object of the present invention to provide an endoscope coupler that may be quickly and easily inserted between an endoscope and a video camera.

Additionally, it is an object of the present invention to provide an endoscope coupler with a rotatable focusing member having improved tactile response when manually moved by an operator to translate a lens assembly sealed within the coupler.

Some of the advantages of the present invention are that the endoscope coupler is: structurally uncomplicated; readily attachable to and detachable from an endoscope and a video camera; easily coupled with diverse types and sizes of video cameras; simple to use by an operator with one hand; and economically feasible.

These and other objects, advantages and benefits are obtained with the endoscope coupler of the present invention as characterized by a cylindrical body having opposing ends attachable to an endoscope and a video camera, respectively, and closed by transparent windows sealing an interior chamber of the body. A lens holder is slidable longitudinally within the chamber and carries a lens for focusing an image to be received by the video camera. Longitudinal keyways are formed exteriorly on the body parallel to a longitudinal axis thereof at 180°-spaced locations. Small permanent drive magnets are angularly spaced exteriorly of the chamber and are slidably disposed in the keyways. The drive magnets are aligned and ferromagnetically coupled to respective permanent driven magnets mounted on the lens holder. Concentrically rotatable about the body is a sleeve having helical slots defined therein to receive the drive magnets. The slots cam the drive magnets when the sleeve is rotated to longitudinally slide the drive magnets within the keyways. As a result of the ferromagnetic coupling, the driven magnets and the lens holder are axially translated within the body. A focusing ring is secured concentrically about the sleeve and coupled therewith to rotate, but not axially translate, relative to the body. The lens holder may thusly be selectively moved within the body in response to rotation of the focusing ring without any mechanical interconnection or linkage between the focusing ring and the lens holder. Retaining rings are disposed on the body in frictional engagement with the sleeve to control rotation of the focusing ring relative to the body and to provide the proper tactile response for an operator manually rotating the focusing ring.

In the preferred embodiment there are two or three stub (i.e., short cylinders) magnets employed as drive magnets disposed at equally spaced (i.e., 180° or 120°) locations about the chamber exterior. Two or three corresponding stub driven magnets are disposed within the chamber, on the lens holder, in radial alignment with respective driven magnets. The manufacturing tolerances on the stub magnets are relatively loose since they have no highly precise fit and location requirements. Accordingly, the drive and driven stub magnets can be mass produced and need not be custom made as in the case of annular magnets. In addition, the drive and driven magnets subtend only small circumferential angles as compared to ring magnets occupying a full 360°. Accordingly, considerably less magnetic material is required for the present invention.

Other objects and advantages of the present invention will become apparent from the following description of the preferred embodiment taken in conjunction with the accompanying drawings wherein like parts in each of the several figures are identified by the same reference characters.

BRIEF DESCRIPTION OF THE DRAWINGS

FIG. 4 is an exploded view in perspective of a second embodiment of an endoscope coupler according to the present invention.

FIG. 5 is a view in longitudinal view section of the endoscope coupler of FIG. 4.

FIG. 6 is a plan view of the endoscope coupler of FIG. 4 coupled to an endoscope and a video camera.

DESCRIPTION OF THE PREFERRED EMBODIMENT

Figure 1:
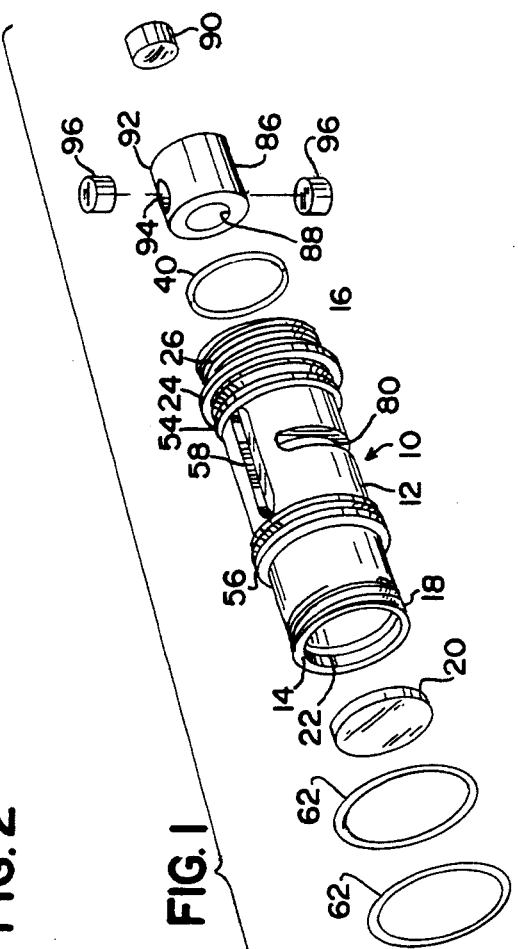
FIG. 1 is an exploded view in perspective of an endoscope coupler according to the present invention.
Figure 2:
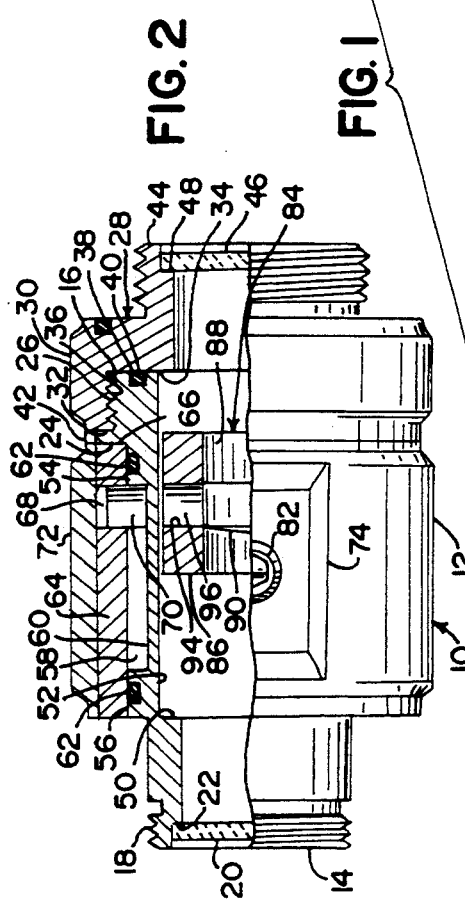
FIG. 2 is a view in longitudinal view section of the endoscope coupler of FIG. 1.
Figure 3:
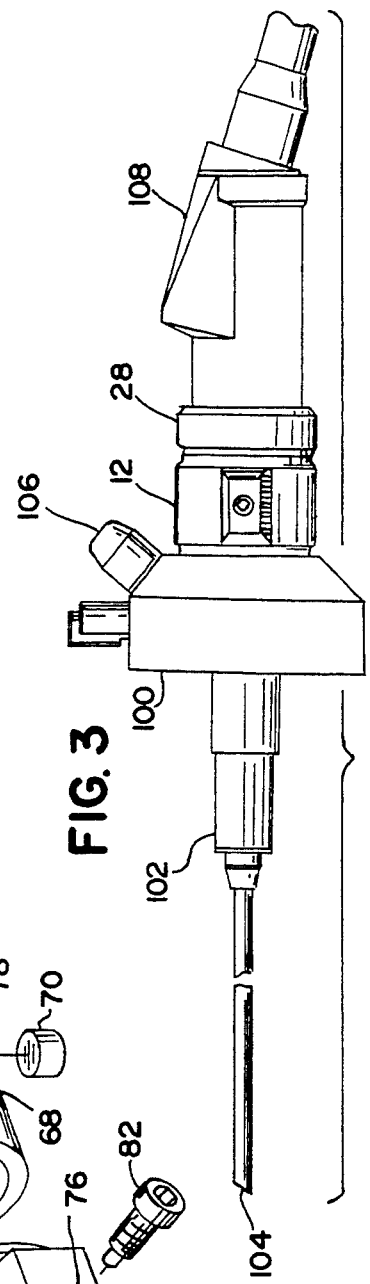
FIG. 3 is a plan view of the endoscope coupler of FIG. 1 coupled to an endoscope and a video camera.

Referring to FIGS. 1-3, an endoscope coupler 10 according to the present invention includes a hollow generally cylindrical body 12 having axially aligned annular ends 14 and 16. The distal end 14 has external threads 18 formed thereon for engagement in an internally threaded passage at a proximal end of an endoscope 102. An inner diameter surface of body 12 adjacent distal end 14 tightly engages the periphery of a transparent window 20 disposed against an annular interior shoulder 22 of the body to close and seal the distal end. An annular flange 24 projects radially outwardly from an outer diameter surface of body 12 at a location longitudinally spaced inwardly from proximal end 16. External threads 26 extend longitudinally from the flange 24 to proximal end 16 for coupling body 12 with an internally threaded adapter 28.

As shown in FIG. 2, adapter 28 includes a cylindrical collar 30 defining an interior annular recess extending longitudinally from an open distal end 32 to an annular wall 34; the recess receives proximal end 16 of body 12. Threads 36 are formed along the entire interior cylindrical surface of the annular recess for engaging threads 26 on proximal end 16 of body 12. An annular groove 38 is formed in end 16 and has a retaining ring 40 disposed therein to be positioned along with end 16 flush against annular wall 34 when body 12 is fully inserted into the annular recess. A peripheral lip 42 on collar end 32 extends axially over the periphery of flange 24 when end 16 is fully inserted into collar 30. End wall 34 extends radially inwardly of an inner diameter surface of body 12 at end 16.

An externally threaded open tubular end 44 extends longitudinally from collar 30 in axial alignment with body end 16 for coupling adapter 28 and, therefore, body 12 with a video camera 108 (FIG. 3). An inner diameter surface of tubular end 44 tightly engages the periphery of a transparent window 46 disposed against an interior annular shoulder 48 oriented normal to a central longitudinal axis of tubular end 42 to close off and seal the tubular end and, therefore, the interior of collar 30 and body 12.

An annular wall 50 is formed on an inner diameter surface of body 12 spaced axially inward from distal window 20. Wall 50 cooperates with wall 34 to define opposing ends of a central, elongated cylindrical passage or chamber 52 within body 12. A raised, annular land 54 projects radially outward from body 12 adjacent and distally of flange 24, and a second similar land 56 projects radially outward from body 12 adjacent and proximally of radially wall 50. Elongated linear keyways 58 are formed in and extend axially along the outer diameter surface of body 12 at 180°-spaced locations between the lands 54 and 56. Webs 60 of non-magnetic material define the bottom walls of the keyways 58. Circumferential grooves are centrally formed in the peripheries of lands 54 and 56, respectively, to receive retaining rings 62 as shown in FIG. 2.

A cylindrical sleeve 64 is concentrically and rotatably disposed over body 12 such that an inner diameter surface of the sleeve is supported on the peripheries of lands 54 and 56 in frictional engagement with the retaining rings 62, and the proximal annular end 66 of sleeve 64 abuts flange 24 of body 12. A pair of arcuately short helical slots 68 are defined through the cylindrical wall of sleeve 64 at 180°-spaced locations. A pair of axially aligned short cylindrical drive magnets 70 have their axes oriented perpendicular to the axis of sleeve 64 and have the outermost portion of their peripheries slidably disposed in slots 68. The innermost portion of the peripheries of magnets 70 are slidably disposed in keyways 58 with the magnet ends disposed against the bottom web 60. Magnets 70 thus extend in radial orientation to the central longitudinal axis of body 12. Slots 68 are oriented in sleeve 64 such that rotation of the sleeve relative to body 12 causes the edges of the helical slots 68 to cam drive magnets 70, thereby producing axial or longitudinal sliding movement of the drive magnets 70 within keyways 58 between lands 54 and 56.

A focusing or actuating ring 72 is disposed concentrically over sleeve 64 in abutting relationship with lip 42 on adapter 28. On the exterior of focusing ring 72 there is formed a raised block 74 having internally threaded hole 76 extending radially toward the central longitudinal axis of body 12. An internally threaded aperture 78 is formed in sleeve 64 in axial alignment with hole 76, and a circumferential track 80 is formed in the cylindrical wall of body 12 in radial alignment with aperture 78. A pin or connecting screw 82 is threadedly insertable through hole 76 and aperture 78 to secure focusing ring 72 to sleeve 64 and permit the sleeve to rotate relative to body 12 simultaneously with the focusing ring 72, while an end of the pin 82 rides in track 80 to prevent longitudinal movement of the sleeve and ring.

A lens assembly 84 is slidably disposed along passage 52 in body 12 and includes a cylindrical lens holder 86 concentrically disposed in passage 52 and having a central axially extending cavity 88. Within cavity 88 is a lens 90 closely held by engagement of the periphery of lens 90 with an inner diameter surface of lens holder 86 so that the lens axis is coaxial with the central longitudinal axis of cavity 88. Generally cylindrical bores 94 are defined in the lens holder at 180°-spaced locations and in radial orientation to the central longitudinal axis of cavity 88. Cylindrical driven magnets 96 are disposed in respective bores 94 to be axially aligned with drive magnets 70. Driven magnets 96 are magnetically coupled with respective drive magnets 70 through webs 60 such that lens holder 86 and lens 90 move longitudinally (i.e., axially) within passage 52 between annular walls 34 and 50 as drive magnets 70 move longitudinally within keyways 58 in response to rotation of focusing ring 72. Preferably, body 12, adapter 28, windows 20 and 46, sleeve 64 and focusing ring 72 are formed and assembled as a water and gas-tight unit preventing fluid communication between the exterior of the endoscope coupler 10 and the interior of body 12 containing lens assembly 84.

In operation, as shown in FIGS. 2 and 3, body end 14 is threaded into an internally threaded tubular passage in a connector 100 at a proximal end of an endoscope 102 having a distal end 104 carrying a lens to be positioned in a body cavity so as to receive light reflected from a site to be observed. A system of relay lenses within the endoscope 102 produces an image of that site for direct viewing via an eyepiece 106 on the connector 100, or for indirect viewing via a video monitor electronically connected with a video camera 108 having an internally threaded tubular passage receiving tubular end 44 of adapter 28. In order to focus an image of the observed site onto the focal plane of video camera 108, focusing ring 72 can be manually grasped by an operator with one hand and selectively rotated clockwise or counterclockwise relative to body 12. Rotation of focusing ring 72 simultaneously rotates sleeve 64 relative to body 12 so that the sides of helical slots 68 cam drive magnets 70 to slide them longitudinally as guided by keyways 58. Drive magnets 70 can thus be selectively cammed for movement between lands 54 and 56 serving as end stops for the drive magnets 70 at opposing ends of keyways 58. Because driven magnets 96 in lens holder 86 are magnetically coupled with drive magnets 70, lens holder 86 and lens 90 also move longitudinally within passage 52 of body 12 in response to rotation of focusing ring 72. Walls 50 and 34 define opposite end stops of passage 52 between which lens holder 86 and lens 90 can be selectively moved to focus an image to be received by the video camera 108. Importantly, focusing ring 72 and sleeve 64 are prevented from moving axially along body 12 by the distal end of set screw 82 engaged in slot 80.

Endoscope coupler 10 is formed as a water and gas-tight unit and can therefore be sterilized utilizing gas or liquid sterilization techniques without the entry of gas or liquid into body 12 that would contaminate windows 20, 46 and lens 90. Drive magnets 70 and driven magnets 96 permit lens holder 86 and lens 90 to be moved by focusing ring 72 without any mechanical linkage or interconnection that would provide an avenue for entry of gas or liquid into body 12. In other words, there is no mechanical connection or linkage through the cylindrical wall of body 12 and no fluid communication during sterilization of endoscope coupler 10 between the wet boundary (i.e. the exterior of body 12 and adapter 28) and the dry boundary (i.e. the interior of body 12 containing lens assembly 84) that would permit gas or liquid to seep into the coupler body interior.

The use of drive and driven magnet pairs at angularly spaced locations around the lens assembly 84 improves cohesiveness between the outer drive magnets 70 and the inner driven magnets 96. In addition, the angularly spaced magnet pairs prevent rotation of the lens assembly 84 within body 12 and separation of the drive and driven magnets when the endoscope coupler 10 is subjected to mechanical shock.

The retaining rings 62 in frictional engagement with sleeve 64 are not required for sealing purposes; however, they provide the proper tactile feel for rotation of focusing ring 72 in accordance with "Kansei" engineering principles by permitting controllable rotation and insuring that ring 72 does not feel too tight or too loose when manually rotated by an operator. End 16 of body 12, threadedly receivable in collar 30 of adapter 28, permits quick and easy connection and disconnection of body 12 and adapter 28, enabling body 12 to be feasibly utilized with a variety of adapters suitable for connection to diverse sizes and types of video cameras. The externally threaded ends 14 and 44 permit endoscope coupler 10 to be readily attached to and detached from connector 100 and video camera 108, respectively, providing significant savings in time and labor when coupler 10 is sterilized separately from connector 100 and video camera 108.

The embodiment illustrated in FIGS. 1-3 utilizes two angularly spaced pairs of drive and driven magnets to control positioning of the focusing lens. It will be appreciated that additional pairs of angularly spaced magnets may be provided, and that positional stability and adjustability is enhanced as the number of magnet pairs increases. On the other hand, economics dictates that the number of magnet pairs be minimized. It has been found that either the two-pair magnet embodiment illustrated in FIGS. 1-3 or a three-pair embodiment will accommodate the function verses economic trade off most optimally. A three-pair embodiment is illustrated in FIGS. 4-6 to which specific reference is now made.

Endoscope coupler 110 includes a hollow cylindrical body 112 having an open distal end 114 adapted to be connected to the proximal end of endoscope 100. In particular, a plurality of locking balls 116 are carried in respective radial bores 118 in body 112 of the coupler, and engage an annular groove (not shown) formed about a male connector of endoscope 100. Although not described and illustrated herein, the male connector of the endoscope is described and illustrated in co-pending U.S. patent application Ser. No. 07/882,395, filed May 13, 1992, and entitled "Endoscope Coupler With Liquid Interface", assigned to the same assignee as the present invention. The disclosure in that patent application is expressly incorporated herein by reference. For present purposes it is sufficient to note that the male connector groove has an arcuate cross-section with a radius of curvature slightly larger than the radius of balls 116. The locking balls are held in the connector groove by an interiorly facing cylindrical surface of a locking sleeve 120. The locking sleeve is retained coaxially about coupler body 112 for axial movement relative to that body. Locking sleeve 120 is biased by a helical spring 122, also disposed about body 112, the bias being toward the distal end of the coupler (i.e., toward the end receiving the male connector of the endoscope). In order to remove the endoscope connector from the coupler end 114, locking sleeve 120 is moved axially along the coupler body 112 (i.e., rightwardly in FIG. 2), thereby allowing the locking balls 116 to be moved radially outward in bores 118 into a radially enlarged distal end of the locking sleeve. This movement of the locking balls is achieved by withdrawing the endoscope connector from recess coupler end 114, thereby causing the moving arcuate surface of the endoscope connector groove to force the balls 116 radially outward into bores 118 with a camming action and permitting complete withdrawal of the endoscope connector. Locking sleeve 120 is similarly moved rightwardly when it is desired to insert the endoscope connector into recess coupler end 114. In such a case, a chamfered annular edge of the connector initially forces the locking balls radially outward into bores 118, the balls being maintained in their outward position by the cylindrical end section of the endoscope connector. Upon radial alignment between the connector groove and bores 118 (i.e., the maximal insertion position of the connector into the coupler end), the locking balls are free to move inwardly and can be so urged by returning locking sleeve 120 to its quiescent position (i.e., to the left in FIG. 2) under the bias of spring 122. Spring 122 is urged against locking sleeve 120 by a focus ring 126 disposed about coupler body 112 and retained thereon by a flange 128 projecting radially outward from body 112 near the proximal coupler end. Disposed concentrically between body 112 and focus ring 126 is a hollow cylindrical sleeve 124 having a helical slot 128 defined entirely through its circumferential wall. Sleeve 128 is axially much shorter than ring 126, the latter extending both forwardly and rearwardly of the sleeve. The helical slot 128 extends over an angle of approximately 360° along the sleeve circumference. A through hole 129 is defined in the sleeve wall adjacent the proximal end of sleeve 124 at an annular location aligned with the proximal end of slot 128. A pin 130 secured to focus ring 126 extends radially through hole 129 and into a circumferential recess 132 defined in body 112 near the proximal end of sleeve 124. The inwardly facing end of pin 130 is free to ride in a circumferential recess 132 in body 112 as focus ring 126 is rotated relative to body 112.

Three recesses 134 are defined in body 112 at respective 120°-spaced locations and extend in a longitudinal direction. Recesses 134 are radially aligned with respective portions of helical slot 128 and sleeve 124. Three drive magnet assemblies 136 are disposed in respective recesses 134 and extend radially outward from the recesses into helical slot 128. Each drive magnet assembly 136 may be a single short cylindrical magnet or a plurality of such magnets disposed in a generally cylindrical casing. In either form, the axis of the magnet assembly cylinder is oriented perpendicular to the axis of body 112. It will be appreciated that, upon rotation of focus ring 126 relative to body 112, pin 130 causes sleeve 124 to rotate with the focus ring. Since the distal end of pin 130 rides in circumferential recess 132, the focus ring 126 and sleeve 124 are able to rotate relative to body 112. Helical slot 128 serves to cam the drive magnet assemblies 136 which are constrained to move only axially by respective recesses 134. Accordingly, rotation of focus ring 126 produces axial movement of the three drive magnet assemblies as these assemblies ride in helical slot 128.

Interiorly of body 112 is a sealed chamber 141 terminated at opposite axial ends by transparent windows 140 (at the distal end of the chamber) and 142 (at the proximal end of the chamber). Inside the chamber, near its proximal end, there is disposed a positionally fixed lens assembly 144 secured in place by a locknut 146 threadedly engaging the bore in body 112 forming chamber 141. The details of fixed lens assembly 144 are not important to the present invention and, accordingly, are not described in detail herein. It is only necessary to note that fixed lens assembly 144 may include one or more lenses disposed in the optical path through the coupler. A moveable lens assembly is disposed forwardedly of fixed assembly 144 and includes a lens holder 148 having cylindrical end portions of a first diameter and a cylindrical intermediate portion of a lesser diameter. The end portion diameters are selected to permit the lens holder to slide longitudinally along the interior surface of body 112 that defines chamber 141. A pair of focusing lenses 150, 151 are fixedly mounted interiorly of holder 148 with their optical axes disposed coaxially with chamber 141. In this arrangement, lenses 150 and 151 are moved axially in chamber 141 as lens holder 148 is moved axially.

Three equiangularly spaced recesses 152 are defined in the outer surface of the proximal cylindrical end portion of lens holder 148. Recesses 152 are general cylindrical in shape and are oriented with their axes perpendicular to the coaxial optical axis and longitudinal axis of chamber 141. Each recess 152 receives a short cylindrical driven magnet assembly 154 in relatively snug fitting relation. Driven magnet assemblies 154, by virtue of the angular spacing of their receiving recesses 152, are mutually spaced by 120°, just as driven magnet assemblies 136 are spaced by 120°. Each driven magnet assembly 154 is radially aligned with a respective drive magnet assembly 136 so that three separate flux paths are established through the portions of magnetically non-permeable body 112 subsisting between the magnet assembly pairs. From the foregoing it will be clear that longitudinal movement of the drive magnet assemblies 136 in response to rotation of focus ring 126 causes corresponding longitudinal movement of lens holder 148 and its internal lenses 150, 151. Accordingly, focus control over the image transmitted through coupler 110 is readily achieved by rotation of focus ring 126.

The short drive and driven magnet of the present invention occupy relatively small circumferential angles around the periphery of bodies 12 and 112. Typically, the magnetic material occupies less than ten percent of the 360° occupied by annular magnets used in the prior art.

Having described preferred embodiments of a new and improved endoscope coupler with magnetic focus control, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An endoscope coupler for mechanically and optically coupling an endoscope to a viewing device, said coupler comprising:

a lens;

a sealed chamber surrounding said lens, said chamber including a peripheral wall disposed about a longitudinal axis and a window permitting light to enter said chamber and said lens;

a lens holder disposed inside said chamber and having a peripheral wall disposed about said longitudinal axis, said lens holder being movable along said longitudinal axis within said chamber and being arranged to cause motion of said lens in said chamber when said lens holder is moved;

driven magnet means supported on said lens holder in said chamber and occupying an angle corresponding to less then ten percent of the peripheral wall of said lens holder;

drive magnet means supported outside said chamber and ferromagnetically coupled to said first driven magnet through a wall of said chamber said drive magnet means occupying an angle less then ten percent of the peripheral wall of said chamber;

a focus control member mechanically linked to said drive magnet means for selectively moving said drive magnet means to thereby move said ferromagnetically coupled driven magnet means longitudinally in said chamber in response to rotation of said focus control member about the longitudinal axis of said chamber;

wherein said ferromagnetic coupling between said drive magnet means and said driven magnetic means occupying said angle opposes both rotation of said lens holder within said chamber and separation of said drive and driven magnet means; and means for preventing longitudinal movement of said focus control member along said longitudinal axis.

2. The endoscope coupler as recited in claim 1 wherein said chamber is generally cylindrical and said lens has an optical axis positioned substantially coaxially with the longitudinal axis of said chamber, and wherein said drive magnet means is an axially short cylindrical permanent first drive magnet assembly having a cylindrical axis oriented perpendicular to the longitudinal axis of said chamber.

3. The endoscope coupler as recited in claim 2 further comprising:

guide means defined in said peripheral wall of said chamber for constraining movement of said drive magnet means to a longitudinal direction relative to said chamber.

4. The endoscope coupler as recited in claim 3 wherein said driven magnet means is an axially short cylindrical permanent first driven magnet assembly having a cylindrical axis positioned coaxially with the cylindrical axis of said first magnet assembly.

5. The endoscope coupler as recited in claim 4 wherein said driven magnet means further comprises an axially short cylindrical permanent second driven magnet assembly supported on said lens holder at a position angularly spaced from said first drive magnet assembly about said longitudinal axis;

wherein said drive magnet means further comprises an axially short cylindrical permanent second drive magnet assembly supported outside said chamber and ferromagnetically coupled to said second driven magnet assembly through said chamber wall; and wherein said focus control member is linked to said first and second drive magnet assemblies for selectively moving said first and second drive magnet assemblies in unison and thereby moving said ferromagnetically coupled first and second driven magnet assemblies and said lens holder in unison longitudinally in said chamber.

6. The endoscope coupler as recited in claim 5 wherein said driven magnet means further comprises an axially short cylindrical permanent third driven magnet assembly supported on said lens holder at a position angularly spaced from said first and and second driven magnet assemblies about said longitudinal axis;

wherein said drive magnet means comprises an axially short cylindrical permanent third drive magnet assembly supported outside said chamber and ferromagnetically coupled to said third driven magnet assembly through said chamber wall; and wherein said focus control member is also linked to said third drive magnet assembly for selectively moving said first, second and third drive magnet assemblies in unison and thereby moving said ferromagnetically coupled first, second and third driven magnet assemblies and said lens holder in unison longitudinally in said chamber.

7. The endoscope coupler as recited in claim 1 further comprising:

guide means defined in said peripheral wall of said chamber for constraining movement of said drive magnet means to a longitudinal direction relative to said chamber.

8. The endoscope coupler as recited in claim 1 wherein said driven magnet means comprises first, second and third axially short cylindrical permanent driven magnet assemblies supported on said lens holder at a position angularly spaced from each other;

wherein said drive magnet means comprises first, second and third axially short cylindrical permanent drive magnet assemblies supported outside said chamber and ferromagnetically coupled to said first, second and third driven magnet assemblies, respectively, through said chamber wall; and wherein said focus control member is linked to said first, second and third drive magnet assemblies for selectively moving said first, second and third drive magnet assemblies in unison and thereby moving said ferromagnetically coupled first, second, and third driven magnet assemblies and said lens holder in unison longitudinally in said chamber.

9. The endoscope coupler as recited in claim 1 wherein said chamber is generally cylindrical and said lens has an optical axis positioned substantially coaxially with the longitudinal axis of said chamber;

wherein said drive magnet means comprises an axially short cylindrical permanent first drive magnet having a cylindrical axis oriented perpendicular to the longitudinal axis of said chamber;

wherein said driven magnet means comprises an axially short cylindrical permanent first driven magnet having a cylindrical axis positioned coaxially with the cylindrical axis of said first drive magnet; and further comprising:

a second permanent driven magnet supported on said lens holder at a position angularly spaced from said first driven magnet about said longitudinal axis;

a second permanent drive magnet supported outside said chamber and ferromagnetically coupled to said second driven magnet through said chamber walls;

wherein said focus control member is linked to said first and second drive magnets for selectively moving said first and second drive magnets in unison, thereby to move said ferromagnetically coupled first and second driven magnets and said lens holder in unison, longitudinally in said chamber;

wherein said second drive magnet is an axially short cylindrical permanent magnet having an axially cylindrical axis oriented coaxially with the cylindrical axis of said first drive magnet; and wherein said second driven magnet is a short cylindrical permanent magnet having a cylindrical axis oriented coaxially with the cylindrical axis of said first driven magnet.

10. An endoscope coupler for mechanically and optically coupling an endoscope to a viewing device, said coupler comprising:

a lens;

a sealed chamber surrounding said lens and having a longitudinal axis, said chamber including a window to permit light to enter said chamber and said lens;

a lens holder disposed inside said chamber, said lens holder being movable with respect to said chamber and being arranged to cause motion of said lens in said chamber when said lens holder is moved;

at least first and second angularly spaced driven magnets disposed in said chamber and supported on said lens holder at positions angularly spaced about said longitudinal axis;

at least first and second drive magnets supported outside said chamber and ferromagnetically coupled to said first and second driven magnets, respectively, through a wall of said chamber; and a focus control member mechanically linked to said first and second drive magnets for selectively moving said drive magnets to thereby move said first and second driven magnets via said ferromagnetic coupling to, in turn, move said lens holder in response to movement of said focus control member;

wherein said ferromagnetic couplings between said drive and driven magnets at said angularly spaced positions oppose both rotation of said lens holder within said chamber and separation of said drive and driven magnet means.

11. The endoscope coupler as recited in claim 10 further comprising:

means for mounting said focus control member for rotation about said longitudinal axis and preventing said member from moving longitudinally along said longitudinal axis; and wherein said first and second drive magnets, said first and second driven magnets and said lens holder move along said longitudinal axis in response to rotation of said focus control member.

12. The endoscope coupler as recited in claim 11 wherein said chamber is generally cylindrical and said lens has an optical axis positioned substantially coaxially with the longitudinal axis of said chamber, and wherein said first and second drive magnets are short cylindrical permanent magnets having respective cylindrical axes oriented perpendicular to the longitudinal axis of said chamber.

13. The endoscope coupler as recited in claim 12 further comprising guide means defined in a wall of said chamber for constraining movement of said first and second drive magnets to a longitudinal direction relative to said chamber.

14. The endoscope coupler is recited in claim 13 wherein said first and second driven magnets are short cylindrical permanent magnets having respective cylindrical axes positioned coaxially with the cylindrical axes of said first and second drive magnets, respectively.

15. The endoscope coupler as recited in claim 10 further comprising guide means defined in a wall of said chamber for constraining movement of said first and second drive magnets to a longitudinal direction relative to said chamber.

16. The endoscope coupler as recited in claim 10 further including means positioned between said chamber and said focus control member in frictional engagement with said focus control member for frictionally opposing rotation of said focus control member relative to said chamber.

17. The endoscope coupler as recited in claim 16 wherein said means for frictionally opposing includes a pair of elastomeric retaining rings disposed about said chamber.

18. The method of providing an adjustable focusing capability in an optical coupler adapted for mechanically and optically coupling an endoscope to a video camera, said method comprising the steps of:

(a) disposing a lens supported by a lens holder in a sealed elongated chamber having a window to permit light to enter said chamber and said lens;

(b) securing a plurality of permanent driven magnets to said lens holder within said chamber at respective angularly spaced locations about the longitudinal axis of said chamber;

(c) supporting a plurality of drive magnets outside said chamber, each drive magnet being ferromagnetically coupled to a respective driven magnet through a wall of said chamber;

(d) permitting rotation of a focus control member about said longitudinal axis while preventing axial movement of said focus control member along said longitudinal axis;

(e) in response to said rotation of said focus control member, axially translating said drive magnets along said longitudinal axis; and (f) in response to said axial translation of said drive magnets, moving said driven magnets and said lens holder axially in said chamber solely as a result of the ferromagnetic coupling between said driven magnets and said drive magnets;

wherein said ferromagnetic couplings between said drive and driven magnets at said angularly spaced positions oppose both rotation of said lens holder within said chamber and separation of said drive and driven magnet means.

* * * * *